US010959751B2

(12) United States Patent
McCarthy (10) Patent No.: US 10,959,751 B2
(45) Date of Patent: Mar. 30, 2021

(54) PIEZOELECTRIC THROMBUS REMOVAL

(71) Applicant: Warren Z McCarthy, Salt Lake City, UT (US)

(72) Inventor: Warren Z McCarthy, Salt Lake City, UT (US)

( * ) Notice: Subject to any disclaimer, the term of this patent is extended or adjusted under 35 U.S.C. 154(b) by 392 days.

(21) Appl. No.: 16/182,606

(22) Filed: Nov. 7, 2018

(65) Prior Publication Data
US 2019/0069922 A1    Mar. 7, 2019

(51) Int. Cl.
*A61B 17/3207* (2006.01)
*A61B 17/00* (2006.01)
*A61B 34/00* (2016.01)

(52) U.S. Cl.
CPC .......... *A61B 17/320758* (2013.01); *A61B 17/00234* (2013.01); *A61B 34/73* (2016.02); *A61B 2017/00345* (2013.01); *A61B 2017/00402* (2013.01); *A61B 2017/00411* (2013.01); *A61B 2017/00876* (2013.01)

(58) Field of Classification Search
None
See application file for complete search history.

(56) References Cited

U.S. PATENT DOCUMENTS

| | | | | |
|---|---|---|---|---|
| 5,728,089 A | * | 3/1998 | Lal | A61B 18/1402 606/1 |
| 7,666,161 B2 | * | 2/2010 | Nash | A61B 17/320783 604/22 |
| 8,834,488 B2 | * | 9/2014 | Farritor | A61B 34/20 606/130 |
| 8,862,205 B2 | * | 10/2014 | Park | A61B 34/72 600/424 |
| 9,743,942 B2 | * | 8/2017 | Beckman | A61B 17/22 |
| 10,058,716 B2 | | 8/2018 | Ma | |
| 2003/0229268 A1 | * | 12/2003 | Uchiyama | A61B 1/00147 600/109 |
| 2007/0038237 A1 | * | 2/2007 | Swayze | A61B 1/00156 606/191 |
| 2007/0138915 A1 | * | 6/2007 | Mulvihill | A61B 17/320758 310/328 |
| 2010/0256518 A1 | * | 10/2010 | Yu | A61B 5/0215 600/562 |
| 2012/0035434 A1 | * | 2/2012 | Ferren | A61B 1/00156 600/301 |
| 2012/0041307 A1 | * | 2/2012 | Patel | A61B 17/320758 600/435 |

FOREIGN PATENT DOCUMENTS

CN    2693434 Y * 4/2005
CN    102151162 A * 8/2011
(Continued)

*Primary Examiner* — Amy R Weisberg (57) ABSTRACT

A miniature motorized cutter is provided to remove an occlusion or thrombus in the vein or artery of a patient. The miniature motorized cutter has a cutting device operated by a piezoelectric motor. The piezoelectric motor is wirelessly powered by electrical induction from outside of the body. The miniature motorized cutter has a positional orienting structure that has two poles of opposite charges. A strong magnet outside of the body can be used to orient the cutter by applying attractive and repulsive forces to the two poles of the positional orienting structure.

2 Claims, 10 Drawing Sheets

(56) References Cited

FOREIGN PATENT DOCUMENTS

| | | | | |
|---|---|---|---|---|
| CN | 207118935 | * | 3/2018 | |
| KR | 101083345 B1 | * | 11/2011 | ............... A61B 6/03 |
| KR | 20130127835 A | * | 11/2013 | |
| KR | 10-2014-0026957 | * | 10/2014 | |
| KR | 101471526 B1 | * | 12/2014 | ..... A61B 17/320758 |
| KR | 10-2019-0069084 | * | 10/2019 | |

* cited by examiner

PIEZOELECTRIC THROMBUS REMOVAL

BACKGROUND

Arterial obstructions, such as arterial plaque or deep vein thrombus, can cause life-threatening consequences. Atherosclerosis is a disease in which plaque along artery walls. Arterial plaque includes fat, cholesterol, calcium, and other substances found in the blood. Plaque can be soft and fluffy but over time it can harden. It can also narrow or completely occlude an artery, limiting or terminating blood flow and possibly killing tissue. Atherosclerosis can cause fatigue, lethargy and shortness of breath. Eventually it can lead to heart attack, stroke, and death. In past decades, atherosclerosis was believed to be cause by fat in the diet and high cholesterol levels. A re-evaluation of that assumptions underlying that belief and more recent research indicate the cause may be linked to inflammation, low HDL cholesterol levels, and high levels of glycated or oxidized LDL cholesterol.

A common treatment for a constricted artery due to a buildup of arterial plaque is an angioplasty followed by insertion of a stent in the artery in an effort to hold it open. In more extreme cases, open hearts surgery is performed to re-route blood flow around the constructed artery through arterial grafts.

A thrombus can form anywhere in the body, although many form in the legs of pregnant or obese patients, persons who are inactive for an extended period of time, airline passengers, and others. A thrombus is rarely treated by surgery due to the inherent dangers of the procedure, but when it is, traditional surgery to physically remove the thrombosis can be utilized. In addition, there has been work in the area of laser and radio frequency ablation of clots. Chemical treatment of clots is available as well.

Each of the prior techniques and structures used to treat occlusions of veins and arteries has disadvantages, and another treatment option is needed.

SUMMARY OF INVENTION

A new tool and method are provided for removing full or partial occlusion of a vein or artery, including occlusion or constriction caused by arterial plaque or occlusion caused by thrombosis. A miniature motorized cutter is provided which can be placed into an artery or vein for remote wireless operation to debride or ablate a constriction or occlusion of an artery or vein. The cutter is powered by a piezoelectric motor to which it is mounted. The motor is in turn mounted to an elongate magnetized shaft with a positive pole and a negative pole. Imaging of the patient allows the miniature motorized cutter to be precisely located. Then its orientation may be adjusted by use of a strong magnet outside of the body that exerts an attractive force on one of said poles and a repulsive force on the other. When the miniature motorized cutter is oriented as desired and, proximate a constriction or occlusion, it can be powered wirelessly by electrical induction provided by an inductive power source located outside of the patient's body adjacent the miniature motorized cutter. The cutter, once powered, reduces the thrombus or occlusion. Imaging allows cutting progress to be monitored. Repeated adjustment of cutter position can be provided by the strong magnet. A tourniquet on one side of the occlusion or constriction will prevent cut portions of the occlusion or constriction from travelling to another location in the body. An aspiration catheter may be used to remove cut, debrided or ablated material from the vein or artery. Then the miniature motorized cutter may be removed. This leaves the patient with a vein or artery that has less or no occlusion or constriction.

DETAILED DESCRIPTION

Figure 1:
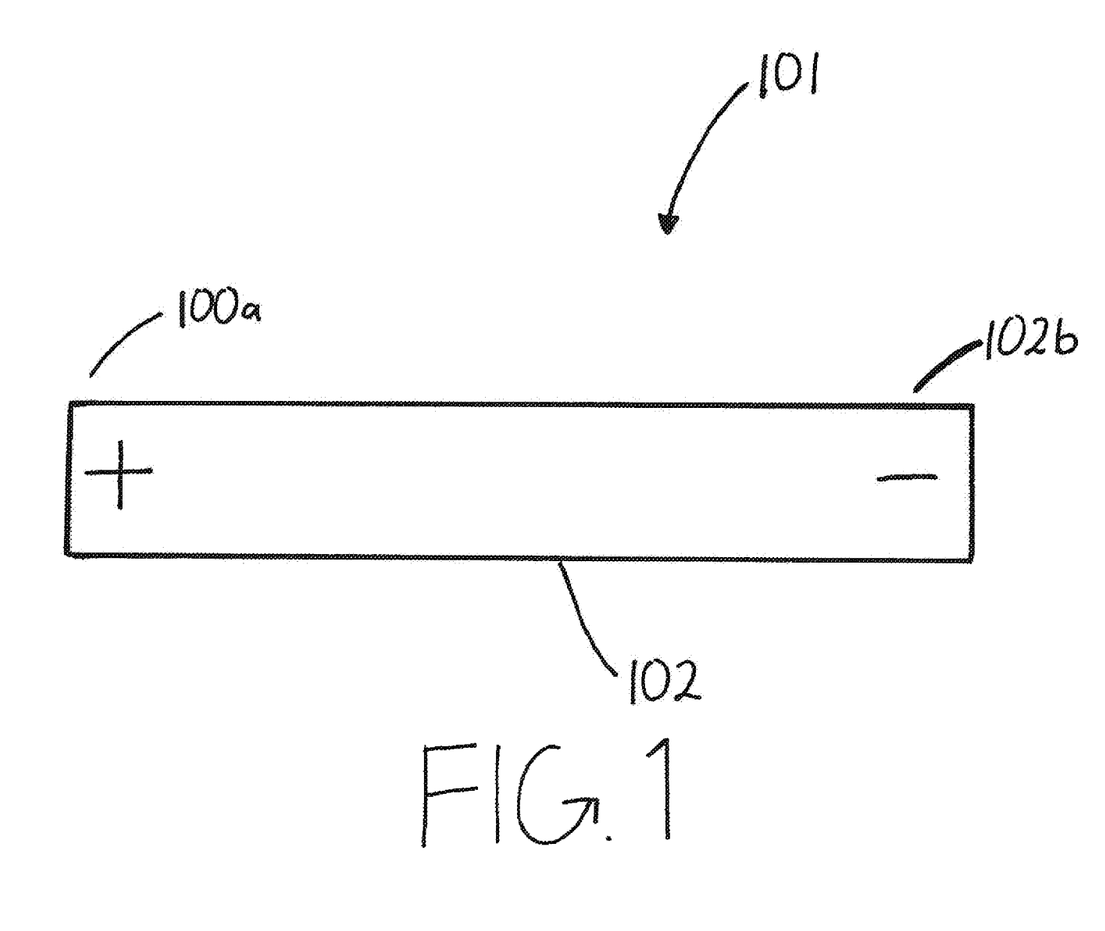
FIG. 1 depicts an elongate conductive shaft.

Referring to FIG. 1 an elongate conductive shaft 101 having a central body 201, an anode 100a and a cathode 102b is depicted. The shaft 101 should be conductive so that it can be influenced by a nearby magnet, and it should be capable of introduction to a human body without toxic effect. The shaft can be a bar, a cylinder, a pipe, elliptical or otherwise.

Figure 2:
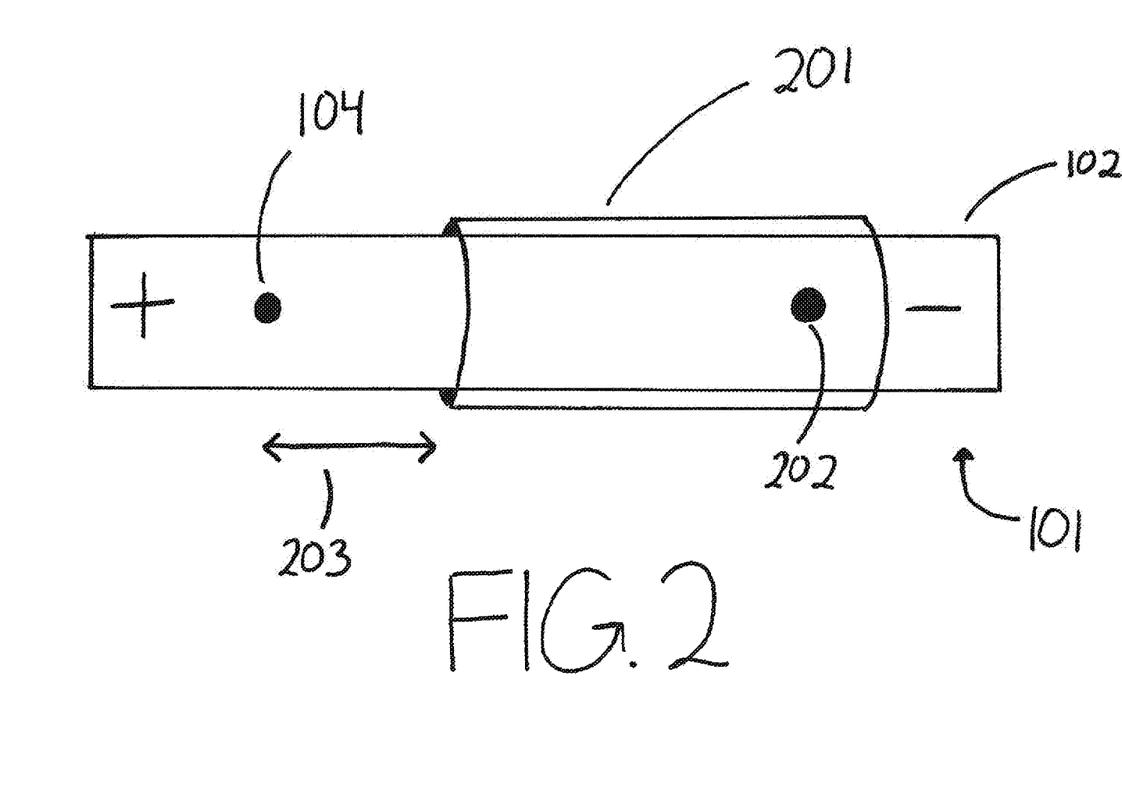
FIG. 2 depicts the elongate shaft of FIG. 1 with a piezoelectric material located on it.

Referring to FIG. 2, the elongate conductive shaft 101 is shown having a drive unit 201 of piezoelectric material 201 mounted on it. The drive unit 201 is mounted to the elongate shaft 101 at mount 202. A fixture 104 is also provided for mounting a cutter (not shown). Then the drive unit 202 is powered with electricity, the drive unit 202 moves in a reciprocating fashion in the direction of arrow 203.

Figure 3:
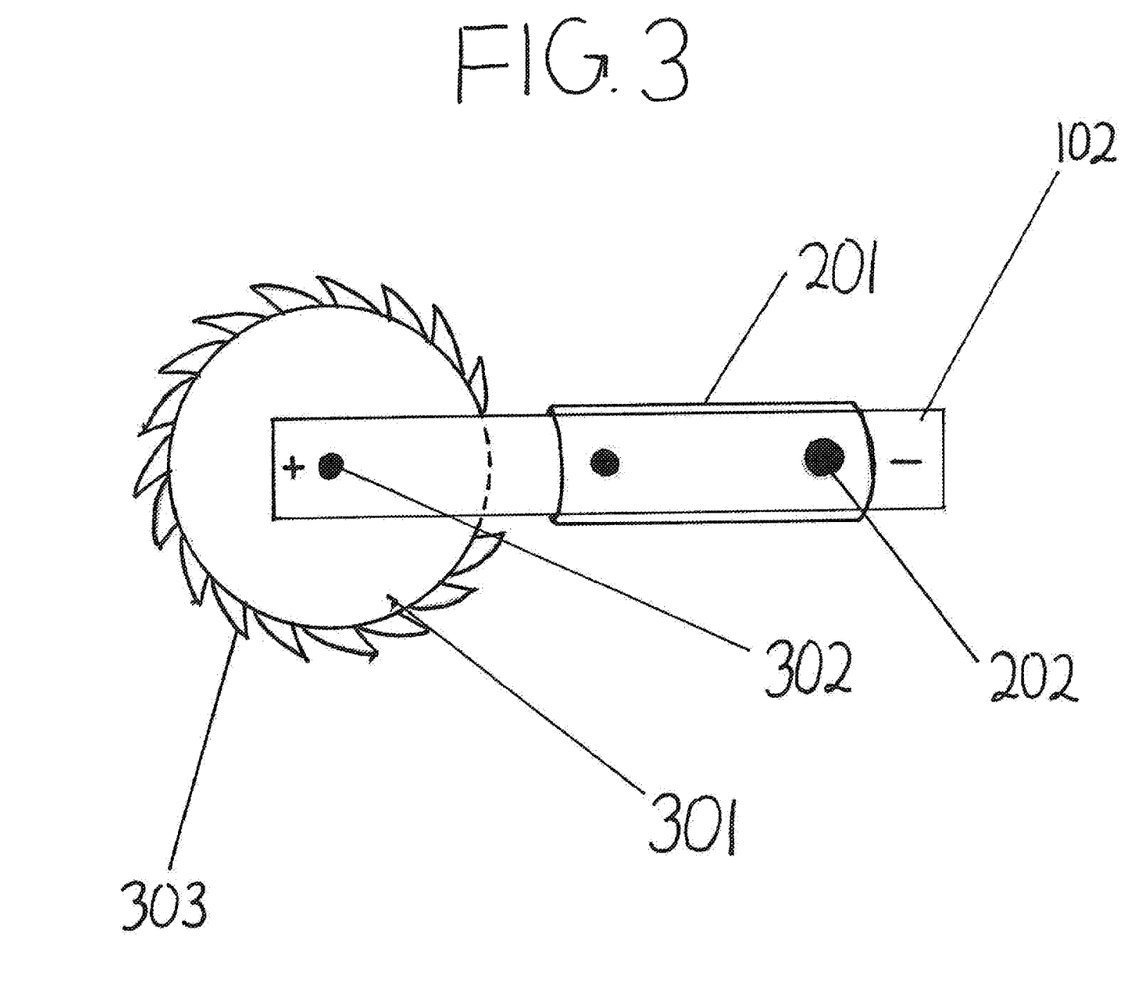
FIG. 3 depicts the elongate shaft of FIG. 2 with a cutter wheel attached.

Referring to FIG. 3, the elongate conductive shaft 102 has a cutter wheel 301 including a plurality of individual cutter blades 302 mounted to the shaft by a centrally-located mounting fixture 302 such as a pin located at fixture 104 (not shown in this figure).

Figure 4:
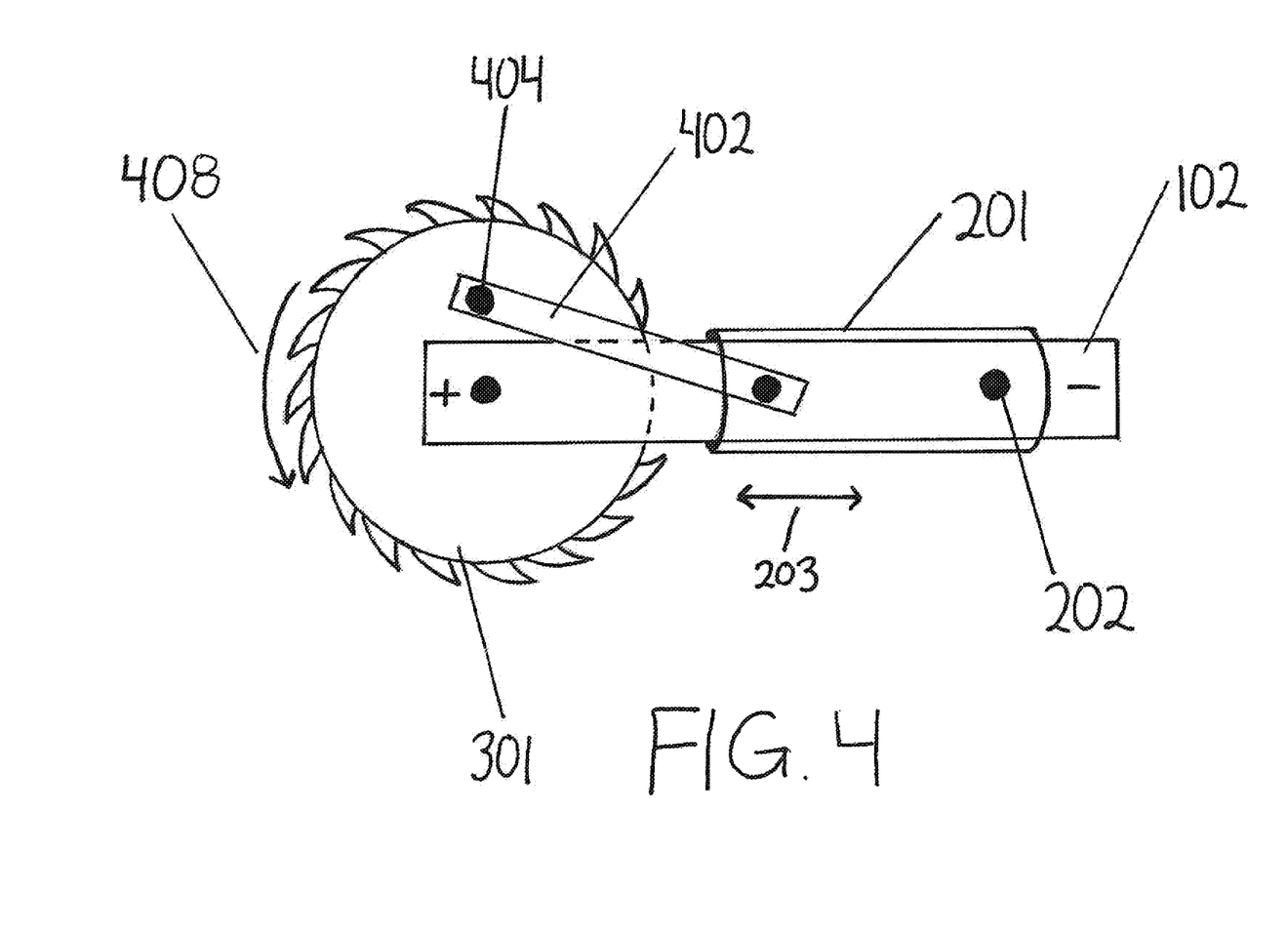
FIG. 4 depicts an assembled miniature motorized cutter having an elongate conductive shaft, a piezoelectric drive unit, a cutter wheel, and a cutter rotation arm.

Referring to FIG. 4, more details of the device of FIG. 3 are provided. FIG. 4 depicts an assembled miniature motorized cutter having an elongate conductive shaft 102, a piezoelectric drive unit 201 a cutter wheel 301, and a cutter rotation arm 402. The arm 402 is attached to the drive unit at its proximal end with mount 403. The arm 402 is attached to the cutter wheel 301 at a location offset from its center by a mount 404. When the drive unit is powered, such as with voltage on then voltage off, the piezoelectric material of the drive unit elongates in the direction of the cutter along the line shown as 203. This in turn moves the arm 402 toward the distal end of the motorized cutter, in turn causing rotation of the cutter wheel 301 in the direction shown by arrow 408. This process can be repeated to cause the cutter wheel to rotate quickly, and when adjacent to material blocking a vein or artery, the cutter wheel can debride, ablate or reduce such material.

Figure 5A:
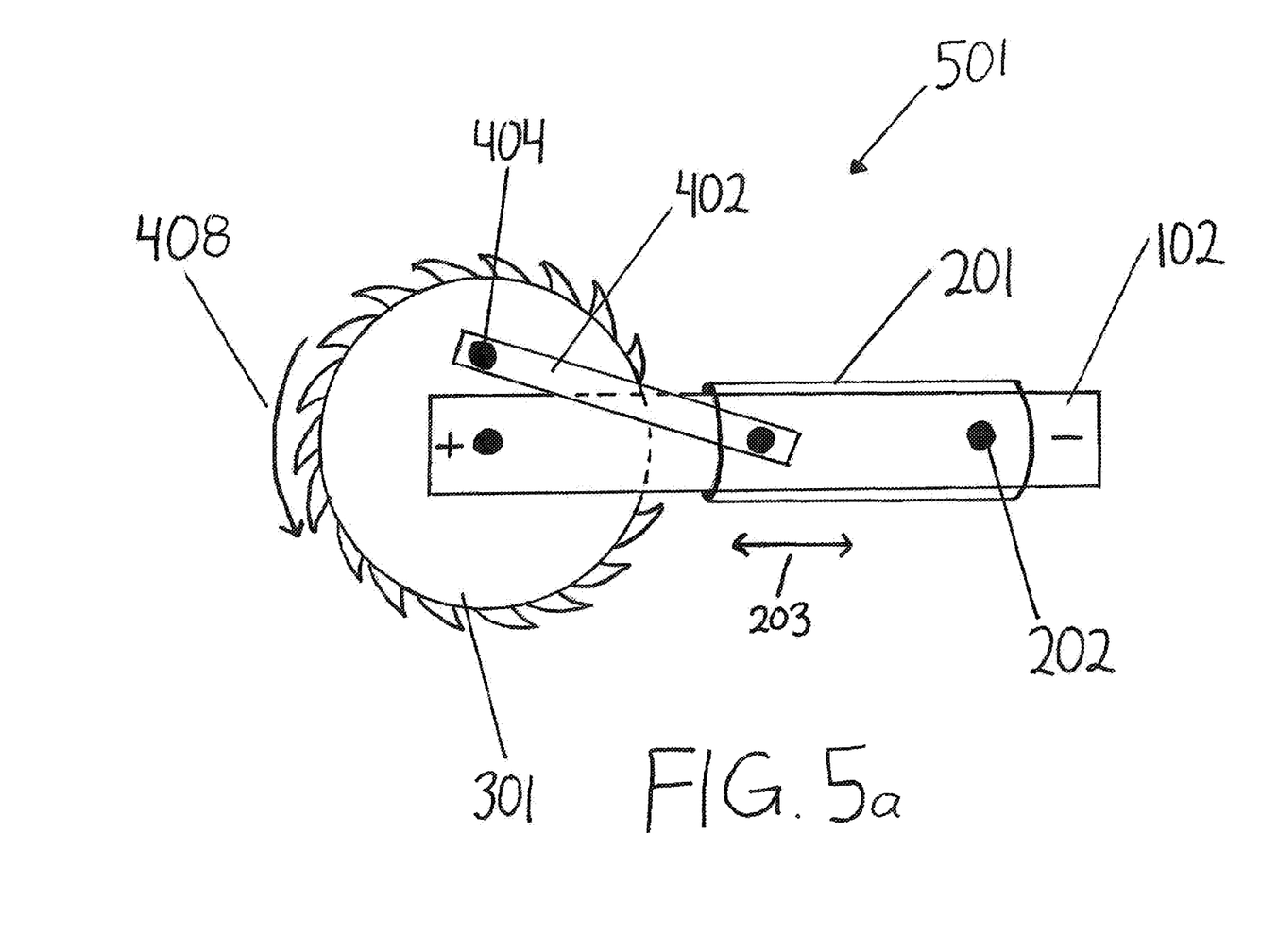
FIGS. 5a, 5b and 5c depict the miniature motorized cutter going through series of cutting motions.
Figure 5B:
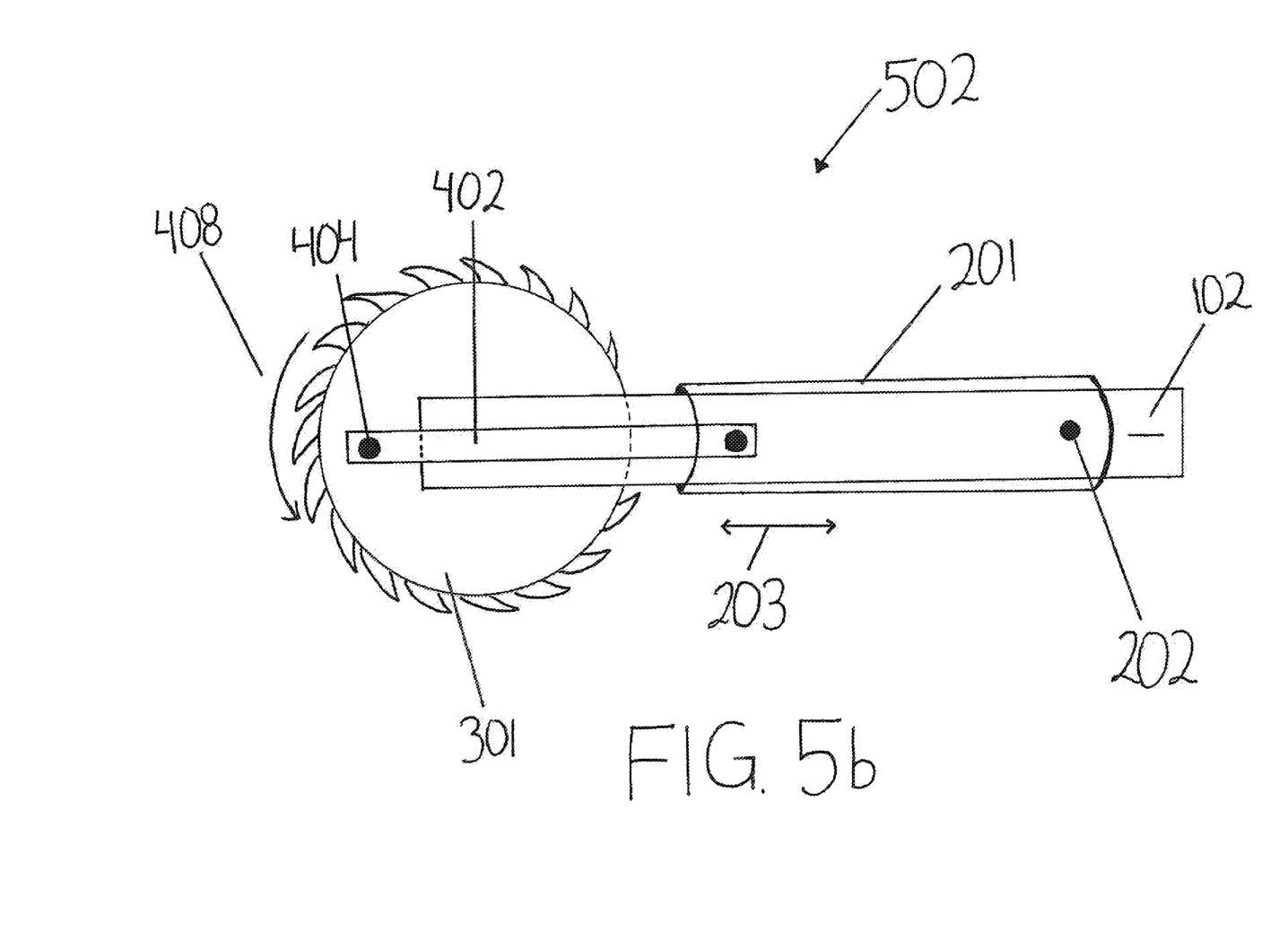
Figure 5C:
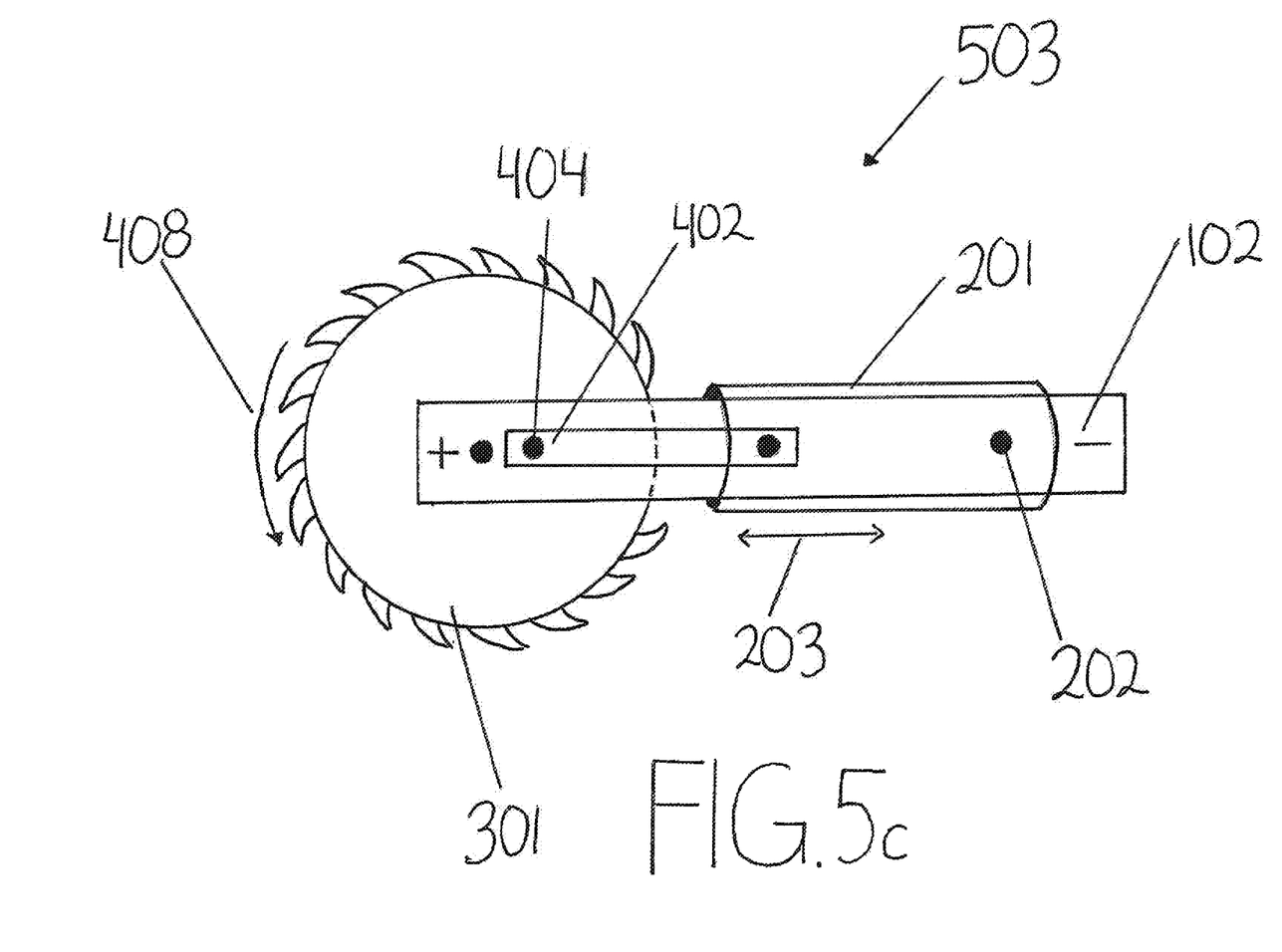

FIGS. 5a, 5b and 5c depict the miniature motorized cutter going through series of cutting motions. When the drive unit 202 is powered, the proximal end of arm 402 extends in the direction of arrow 203 to turn the wheel 301. The three figures highlight motion of the arm 402 to turn the wheel 301. The figures show the device in three states 501, 502 and 503, with the cutter wheel and its arm in three different positions, based on piezo movement.

Figure 6A:
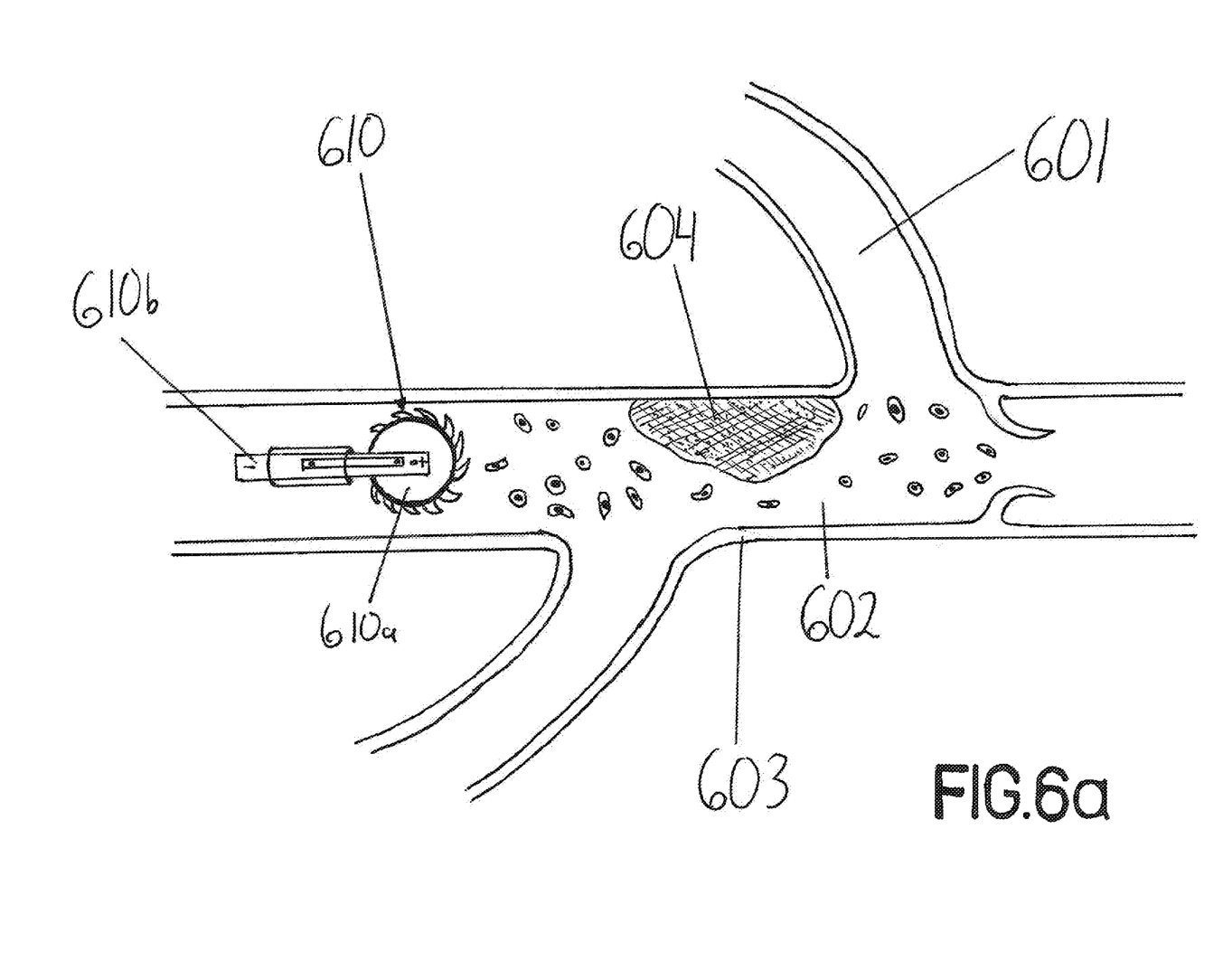
FIG. 6a depicts a miniature motorized electric cutter in use within a human body.

FIG. 6a depicts a miniature motorized electric cutter in use within a human body. First, a physician must determine the location of an occlusion or thrombus 604 to be reduced or ablated with the invented method and device. Then the physician should use a tourniquet (not shown) past the occlusion or thrombus 604 to create and end point beyond which the cutter cannot travel. Next the physician must access the vein or artery 601 in order to insert the miniature motorized cutter. The vein or artery 601 has an inner passage 602 and a wall 603. The cutter can travel within the passage 602 but is confined by the wall 602. Such access can be performed with traditional methods such as use of a scalpel or catheter. The miniature motorized cutter 610 has a 610a and a tail 610b along its elongate shaft. One of the head or tail has a positive charge and the other has a negative charge defining a miniature motorized cutter axis 650.

Figure 6B:
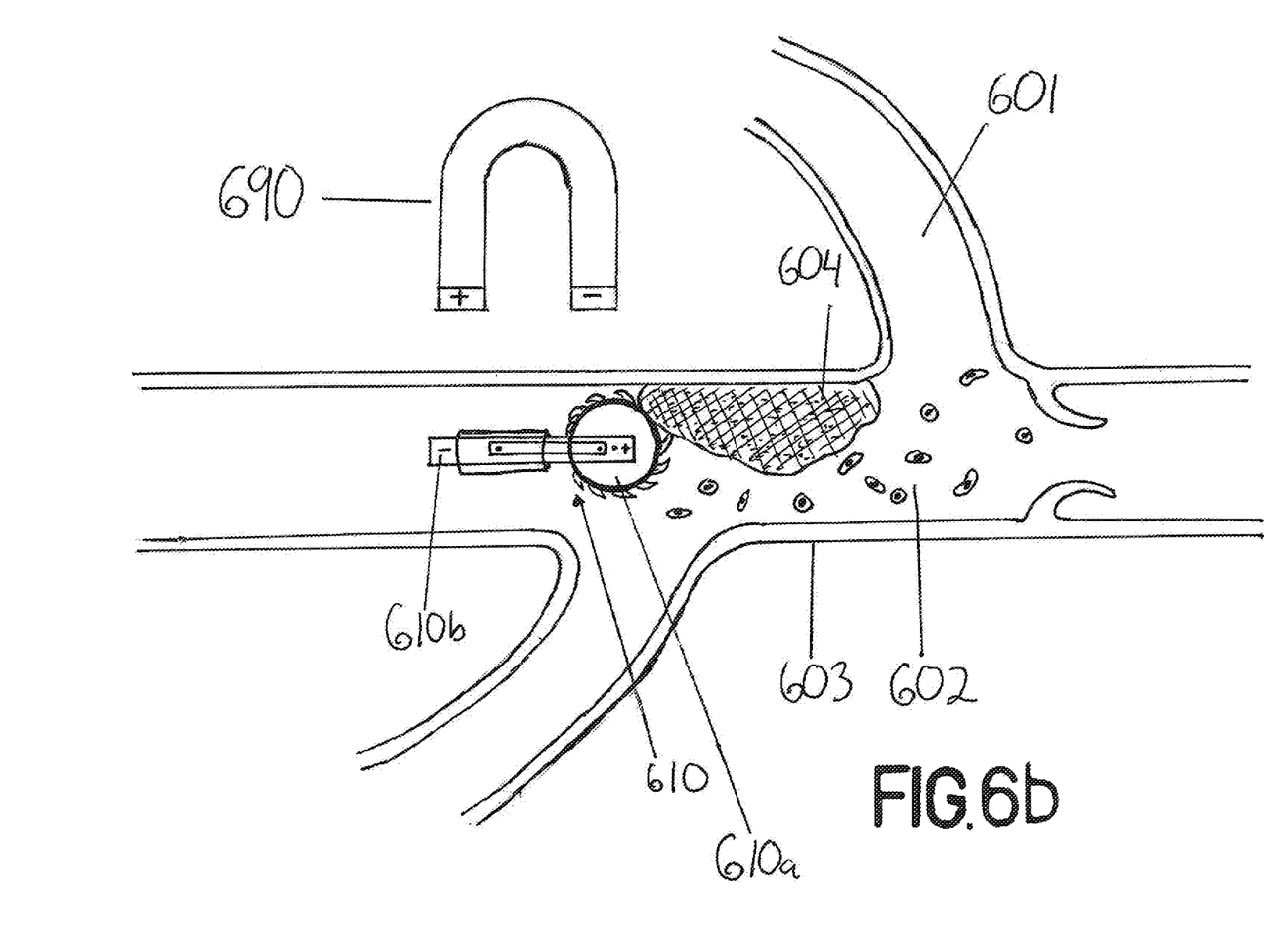
FIG. 6b depicts locating a miniature motorized cutter adjacent to an occlusion or thrombus within a vein or artery.

Referring to FIG. 6b, the next step is to use a magnet to draw the miniature motorized cutter 610 along the vein or artery in the direction of its axis 630 until it reaches a location adjacent to the occlusion or thrombus 604. A magnet 690 (shown figuratively) may be used to do this. Magnets are well known in the medical field and are not explained in detail here. Then a magnet is used to exert a push on one pole of the elongate shaft of the miniature motorized cutter and a pull on the other pole in order to orient the cutting wheel of the miniature motorized cutter adjacent to the thrombus or occlusion.

Figure 6C:
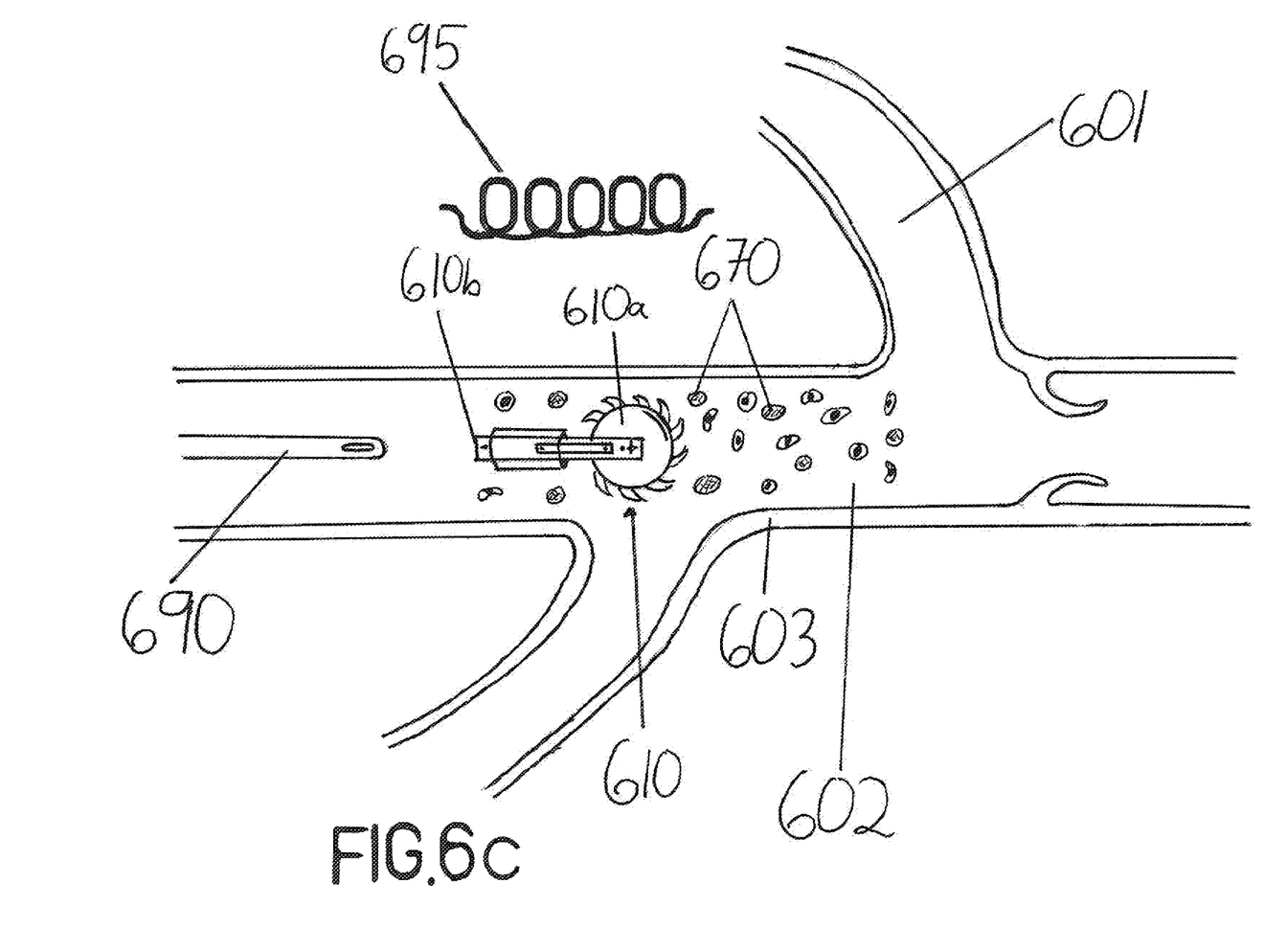
FIG. 6c depicts use of a miniature motorized cutter to ablate a thrombus.

FIG. 6c depicts use a a miniature motorized cutter 610 to ablate a thrombus 604. The miniature motorized cutter 610 is powered by powering an induction coil 695 about or adjacent to the portion of the body where the thrombus 604 is located. Powering the induction coil causes the piezoelectric drive unit to reciprocate within moves the cutter arm and turns the cutter wheel. The cutter wheel ablates the thrombus 604 leaving particles 670 of ablated thrombus or ablated occlusion. Then an aspiration catheter 690 can be used to remove the ablated thrombus or occlusion from the vein or artery. This may be performed repeatedly with saline washes to remove all material. Supplemental imaging may be needed for good effect. The miniature motorized cutter and tourniquet is removed and the patient can recover.

The invention depicted herein is merely illustrative of the concept of the invention. The invention may be implemented by other techniques, steps or structures. For example, rather than using a cutter arm to turn the cutter wheel, the cutter could be turned by a pawl. Or the cutter could have a drive gear driven by a differential motion between to plates where one plate is affixed to the piezoelectric drive unit and the other is not. Other arrangements are possible as well.

The piezoelectric drive unit operates based on the change in shape of a piezoelectric material when an electric field is applied. An electrical circuit makes acoustic or ultrasonic vibrations in the piezoelectric material, which produce linear or rotary motion. In this mechanism, the elongation in a single plane makes a series of stretches and position holds, analogous to the way a caterpillar moves.

In the example implementation depicted above, a wireless piezeoelectric configuration is used in order to facilitate transport of the miniature motorized piezoelectric cutter deep within the human body to access difficult to reach occlusions. Use of a magnet to navigate the miniature motorized cutter to its destination allows addressing occlusions not accessible by traditional catheter access.

The piezoelectric drive unit of the invention can be powered by wireless current induction using an induction coil which is known in the field of electrical engineering. An induction coil creates a rapidly changing magnetic field which induces a current along the elongate conductive shaft of the miniature motorized cutter. That current powers the piezoelectric drive unit that in turns causes the cutter wheel to rotate to provide a cutting effect. Alternatively, electrical wires could be attached to the miniature motorized cutter in order to provide wired access to a power source located outside of the patient's body.

In an alternative embodiment of the invention, an ultrasonic motor can be used instead of a piezoelectric transducer. The reciprocating motion of the ultrasonic motor can be converted to rotational motion of the cutter by known techniques. The ultrasonic motor can be powered by providing traveling-wave vibration or standing-wave vibration outside of the patient's body in a location adjacent to the ultrasonic motor in order to cause such reciprocating motion.

For ease of reference, the term venous passage shall refer to both veins and arteries, and the term occlusion shall refer to an occlusion, a thrombus, arterial plaque or any other material restricting blood flow.

The invention claimed is:

1. A method for ablating an occlusion in a vein or artery of a patient comprising the steps of:
    locating the occlusion,
    placing a tourniquet on said patient on one side of said occlusion,
    gaining access to a venous passage leading to said occlusion,
    placing a miniature motorized cutter within said venous passage,
        said miniature motorized cutting including
    an elongate conductive shaft having a positive pole at one end and a negative pole at its other end,
    a piezoelectric drive unit mounted to said shaft in a configuration such that when piezoelectric material of said piezoelectric drive unit receives electrical power, it expands in size along said elongate conductive shaft,
    a cutting wheel mounted to one end of said elongate conductive shaft,
    an arm mounted to said piezoelectric drive unit and to said cutter so that when said piezoelectric drive unit expands in size along said elongate conductive shaft, said arm causes said cutting wheel to rotate so that it may cut an occlusion,
    using a magnet located outside of the patient's body to cause said miniature motorized cutter to move to a location adjacent said occlusion,
    using a magnet located outside of the patient's body to orient said miniature motorized cutter so that said cutting wheel is located adjacent said occlusion where said cutting wheel may be rotated in order to cut said occlusion,
    placing an induction coil outside of said patient's body in a location where it can inductively power said miniature motorized cutter by inducing a current along said elongate conductive shaft in order to power said piezoelectric drive unit so that said piezoelectric drive unit expands along said conductive elongate shaft in order to articulate said arm and turn said cutting wheel,
    inductively powering said miniature motorized cutter in order to satisfactorily ablate said occlusion,
    removing ablated occlusion material from said venous passage,
    removing said miniature motorized cutter from said venous passage, and
    allowing said patient to recover.

2. A method for ablating an occlusion in a vein or artery of a patient comprising the steps of:

locating the occlusion, placing a tourniquet on said patient on one side of said occlusion, gaining access to a venous passage leading to said occlusion, placing a miniature motorized cutter within said venous passage, said miniature motorized cutting including an elongate conductive shaft having a positive pole at one end and a negative pole at its other end, a piezoelectric drive unit mounted to said shaft in a configuration such that when piezoelectric material of said piezoelectric drive unit receives electrical power, it expands in size along said elongate conductive shaft, a cutting wheel mounted to one end of said elongate conductive shaft, an arm mounted to said piezoelectric drive unit and to said cutter so that when said piezoelectric drive unit expands in size along said elongate conductive shaft, said arm causes said cutting wheel to rotate so that it may cut an occlusion, positive and negative wire leads on said piezoelectric drive unit for receiving electrical power from a wired power source located outside of the patient's body, using a magnet located outside of the patient's body to cause said miniature motorized cutter to move to a location adjacent said occlusion, using a magnet located outside of the patient's body to orient said miniature motorized cutter so that said cutting wheel is located adjacent said occlusion where said cutting wheel may be rotated in order to cut said occlusion, electrically powering said miniature motorized cutter in order to satisfactorily ablate said occlusion, removing ablated occlusion material from said venous passage, removing said miniature motorized cutter from said venous passage, and allowing said patient to recover.

* * * * *